United States Patent [19]
Koenig

[11] Patent Number: 5,037,440
[45] Date of Patent: Aug. 6, 1991

[54] ORTHOPEDIC TOE IMPLANT

[75] Inventor: Richard D. Koenig, Creve Coeur, Mo.

[73] Assignee: Koenig Implant, Inc., Bridgeton, Mo.

[21] Appl. No.: 362,165

[22] Filed: Jun. 6, 1989

[51] Int. Cl.$^5$ .............................................. A61F 2/42
[52] U.S. Cl. ..................................................... 623/21
[58] Field of Search ....................... 623/21, 16, 18, 19, 623/20, 21, 23

[56] References Cited

U.S. PATENT DOCUMENTS

| | | |
|---|---|---|
| 4,156,296 | 5/1979 | Johnson .................................. 623/21 |
| 4,205,400 | 6/1980 | Shen et al. . |
| 4,231,121 | 11/1980 | Lewis . |
| 4,242,759 | 1/1981 | White . |
| 4,353,136 | 10/1982 | Polyzoides et al. . |
| 4,568,348 | 2/1986 | Johnson et al. ........................ 623/20 |
| 4,642,122 | 2/1987 | Steffee . |
| 4,650,490 | 3/1987 | Figgie . |
| 4,731,087 | 3/1988 | Sculco et al. . |

FOREIGN PATENT DOCUMENTS

8906947  8/1989  World Int. Prop. O. ............ 623/20

Primary Examiner—David J. Isabella
Attorney, Agent, or Firm—Armstrong, Teasdale, Schlafly, Davis & Dicus

[57] ABSTRACT

A prosthetic joint for replacing a metatarsal-phalangeal joint of a human toe has a head with a convex bearing surface that moves against the concave bearing surface of a base. The base is elliptical and formed by two different radii of curvature with a desired ratio. The head has a generally concave bone confronting surface with four different generally flat surface areas, one surface is horizontal and parallel to the longitudinal axis of the metatarsal bone, another extends approximately perpendicular thereto, and two others extend at angles to the longitudinal axis. The horizontal lower surface allows better distribution of vertical force and helps to resist separation of the head from the bone. The head exterior surface has four different regions formed by four different radii of curvature with desired ratios to one another. These four head surfaces allow the head and base to reproduce pivoting of a healthy toe joint. A method for installing the prosthetic joint is also disclosed.

37 Claims, 2 Drawing Sheets

ORTHOPEDIC TOE IMPLANT

BACKGROUND OF THE INVENTION

This invention relates to a surgical prosthetic joint designed to replace a metatarsal-phalangeal articulation of a human toe, and methods of its installation.

Various types of prosthetic joints have been developed to replace diseased or damaged human toes. Toe joint prosthesis are known in the art and commonly comprise two components having opposed ball and socket parts. A metatarsal component of the prosthetic joint is designed to be surgically implanted on the end of a resected metatarsal bone of the joint being replaced. A phalangeal component of the prosthetic joint is designed to be surgically implanted at a resected end of a phalanx bone of the joint being replaced. The metatarsal component is commonly constructed from a metal alloy and provides a convex bearing surface to replace and function as the original convex surface of the metatarsal bone of the toe joint. The phalangeal component has a concave surface that slides over the convex surface of the metatarsal component and is designed to replace and function as the original socket surface of the phalanx bone of the toe joint. In the prior art, the metatarsal component and the phalangeal component have been secured to the resected ends of the metatarsal and phalangeal bones such as with pegs or pins that extend from the components opposite their respective ball and socket surfaces. In the art, the pegs or pins fit with the bones to hold the prosthetic joint components in their proper positions relative to the metatarsal and phalangeal bones.

In preparation for the implantation of conventional prosthetic joints, the end of the metatarsal bone of the joint to be replaced is resected to dimensions that provide a close fit between the metatarsal component of the prosthetic joint and the resected end of the metatarsal bone. The phalanx bone of the joint being replaced is also resected to dimensions that provide a close fit between the phalangeal component of the prosthetic joint and the resected end of the phalanx bone. A groove or hole can be cut into each of the resected ends of the bones, to receive the above discussed peg or pin protrusions of the metatarsal and phalangeal components. The metatarsal and phalangeal components of the prosthetic joint are implanted in their proper positions on the resected ends of the respective metatarsal and phalanx bones. This is done by inserting the protrusions of the components into the cuts made in the ends of the respective bones and cementing the components in place.

When a metatarsal bone of a joint is diseased or injured to the extent that it requires replacement with a prosthetic joint, often the top dorsal surface and the bottom plantar surface of the metatarsal bone are also diseased or injured. These surfaces must be replaced to provide for a full range of articulating movement of the phalanx bone relative to the metatarsal bone. However, some prior art prosthesis provide a metatarsal component with a convex bearing surface that does not extend far enough up over the top of the resected metatarsal, or far enough down under the bottom of the resected metatarsal, to replace the diseased or injured dorsal and plantar surfaces of the metatarsal bone.

Also, many of the known prosthetic joints designed to replace the metatarsal-phalangeal articulation of the human toe have a metatarsal component with a bone confronting surface angled from the horizontal that confronts and is cemented to a resected bottom surface of the metatarsal bone. These prior art metatarsal components provide either very little or no horizontal surface area of contact between the metatarsal component of the prosthesis and the resected metatarsal bone to distribute the force exerted on the metatarsal component from walking over an area of the metatarsal bone. Also, the angled surfaces of some prior art prosthesis metatarsal components resolve the force exerted on the metatarsal component from walking into vertical and horizontal components of force. This results in the horizontal component of force tending to separate the metatarsal component of the prosthesis from the metatarsal bone, and requires that the metatarsal component of the prosthesis be cemented in place, or that some other measures be taken to ensure that the component does not separate from the bone. In addition, many of the pegs or pins provided on the metatarsal and phalangeal components of the prior art prosthetic joints do not adequately resist torsion forces exerted on the components. These prosthesis components can become loose with time and can cause problems with one surface of one of the prosthetic components sliding over a surface of the other prosthetic component that is not properly oriented relative to the one component.

The present invention overcomes the shortcomings of existing prosthesis. The present invention provides a prosthetic joint that replaces the metatarsal-phalangeal articulation of a human toe and resists torsion forces applied to the prosthetic joint. The present invention further has a horizontal bone confronting surface that distributes the forces exerted on the metatarsal component over a greater area of the metatarsal bone. Moreover, the present invention provides a metatarsal component with an extended bearing surface adapted to extend above and below the resected end of a metatarsal bone to reproduce the extent of articulation of the phalanx bone relative to the metatarsal bone in a healthy toe joint.

It is therefore an object of the present invention to provide an improved human toe prosthetic joint for metatarsal-phalangeal articulation that resists torsion. It is an object for such a toe prosthetic joint to reduce the effect of force applied to the metatarsal through walking by distributing the force over a greater area of the metatarsal. Moreover, it is an object for such a toe prosthetic joint to provide an extended range of articulation of the phalanx bone relative to the metatarsal bone.

SUMMARY OF THE INVENTION

The prosthetic joint of the present invention is designed to replace a diseased or injured metatarsal-phalangeal articulation of a human toe. The prosthetic joint comprises two components, a one-piece metatarsal component or head member, and a one-piece phalangeal component or base member.

The base member of the prosthetic joint is constructed of a plastic such as polyethylene. The base member has an elliptical cross section with an operative bearing surface that is concave and emulates the socket surface of the joint being replaced by the prosthesis. The base member has a flat surface opposite the concave bearing surface. A tapered stem projects perpendicularly from the center of the flat surface of the base member, and a titanium washer or spacer is provided on the flat surface. The spacer is inserted between the base member and the resected phalanx bone and prevents abrasion of the base member from the bone. The spacer has an outer boundary that is co-extensive with the elliptical outer boundary of the base member, and has a hole at its center to permit the base member stem to extend through the spacer.

The head member of the prosthetic joint has a convex operative bearing surface designed to emulate the ball surface of the original joint of the toe the prosthesis is replacing. The convex bearing surface of the head member is a combination of four continuous areas, with each surface area extending across the width of the bearing surface. A vertical center line over the four surface areas forms a continuous curve having four different radii of curvature. The first surface area of the head member bearing surface extends from a horizontal line across the forward most portion of the bearing surface upward and back a sufficient extent to provide a bearing surface area that is arranged to overlap a dorsal portion of a resected metatarsal bone implanted with the prosthesis of the present invention. This extended bearing surface area permits articulation of the phalanx bone upward across the first surface area to emulate the upward pivoting movement of a human toe. The second bearing surface area extends from the line representing the forward most portion of the bearing surface downward to a second line across the width of the surface that is arranged to be just below the bottom surface of a resected metatarsal implanted with the prosthesis of the present invention. The third bearing surface area extends from this second line across the bottom of the head member to a third line across the width of the bearing surface that is a given distance behind the second line. The third surface area is the lowest area of the bearing surface and receives the forces exerted on the head member from walking. The fourth bearing surface continues from the third line and curves upward to the rearwardmost edge of the head member bearing surface that is arranged to lay adjacent: to a bottom resected surface of a metatarsal bone implanted with the prosthesis of the present invention. The four surface areas of the head member bearing surface provide an extended convex bearing surface area that maintains contact with the operational concave surface area of the base member for all angles of articulation of the base member relative to the head member. The radii of curvature have their centers strategically placed, and the radii lengths have certain ratios to one another that are desirable.

The prosthesis head member is also provided with a concave interior surface that is adapted to confront a resected metatarsal bone of a toe joint implanted with the prosthesis of the present invention. The bone confronting surface of the head member comprises a first planar surface area arranged to extend perpendicular to a longitudinal axis of a metatarsal bone implanted with the prosthesis of the present invention. A stem projects perpendicularly from the first surface area and is arranged to be inserted into a hole bored into a resected end of a metatarsal bone to secure the head member to the bone. Second and third surface areas extend at an angle above and below the first surface area respectively. The second surface area is arranged to overlap the dorsal portion of a metatarsal bone implanted with the prosthesis, and the third surface area is arranged to extend below the bottom edge of a resected metatarsal implanted with the prosthesis head member. A fourth horizontal surface area extends back from the third surface area and presents a horizontal surface arranged to confront beneath a horizontal resected plantar surface beneath the metatarsal.

The first, second, third and fourth surface areas of the concave bone confronting surface of the head member are arranged to provide four planar surfaces that confront four surfaces of a resected metatarsal bone implanted with the head member. The four surface areas prevent the torsion exerted on the head member from normal walking from twisting the head member out of its position relative to the metatarsal bone.

The fourth surface area of the head member is designed to distribute the forces acting on the prosthesis head member from normal walking over a increased area of the metatarsal bone implanted with the prosthesis of the present invention. The vertical component of the force exerted on the head member from walking is reduced by its being distributed over the area of the metatarsal contacted by the fourth surface area of the head member. The horizontal component of the force exerted on the head member from walking that would tend to separate the head member from the metatarsal, is reduced by a counteracting force. This counteracting force is produced by the connection between the head stem and the bore hole in the metatarsal it is inserted into, and by the contact between the horizontal surface section of the bone confronting surface of the head member and the underside of the resected metatarsal implanted with the prosthesis. Because these forces resist the separation of the head member from the bone, it is not necessary for the head member of the prosthesis of the present invention to be cemented in place on the resected end of the metatarsal. Rather, the head member is press fit in place. The base member of the prosthesis is also press fit into position on the resected end of the phalanx bone of the toe joint.

Prior to implantation of the head member and base member of the prosthesis of the present invention, the metatarsal bone and the phalanx bone of the toe joint to be replaced must be properly resected to accommodate the implantation of the head member and base member. A specialized set of tools is provided to facilitate the resection of the metatarsal and phalanx bone.

The phalanx bone is prepared for implantation of the base member of the prosthesis by resecting the end of the bone proximate to the joint being replaced. The bone is resected to present a flat surface at the end of the bone that is perpendicular to the longitudinal axis of the bone. The specialized tools include a set of three elliptical templates having three sizes, small, medium and large. An elliptical template is chosen that most closely approximates the cross sectional area of the flat surface of the resected phalanx bone. Each of the elliptical templates has a hole bored through its center. The template chosen is positioned flat against the resected end of the phalanx bone and a centering hole is drilled into the phalanx bone by drilling through the center hole of the template.

The specialized set of tools also includes a set of three trapezoidal shaped punches. The sizes of the punches also range through small, medium and large. The punch selected is positioned over the hole previously drilled at the center of the phalanx bone and is then impacted into the center of the phalanx bone to produce a trapezoid shaped hole in the center of the bone that is 10% smaller than the stem of the base member chosen to be implanted on the phalanx bone.

The specialized tools also include three metatarsal bone templates ranging in sizes of small, medium and large. The metatarsal templates are adapted to be pinned to the side of the metatarsal bone to be resected and present four guide surfaces. The first guide surface is arranged perpendicular to the longitudinal axis of the metatarsal bone. The second and third surfaces extend above and below the first surface respectively, at angles that are equal to the angles that the second and third surface areas of the bone confronting surfaces of the selected head member of the prosthesis form with the first surface area of the bone confronting surfaces of the head member. The fourth guide surface is arranged parallel to the longitudinal axis of the metatarsal bone. It provides a guide for the resection of the bottom surface of the metatarsal to produce the resected horizontal surface of the bone. This bone surface confronts the fourth surface area of the bone confronting surfaces of the prosthesis head member. The chosen metatarsal template is pinned to the side of the metatarsal bone and the bone is resected to present a first vertical surface at the end of the bone that is perpendicular to the longitudinal axis of the bone, second and third planar surfaces extending above and below the first surface at the desired angles, and a fourth surface beneath the bone that is parallel to the longitudinal axis of the bone.

An additional set of three resection gauges are provided for the resected metatarsal bone. These gauges are arranged in sizes of small, medium and large, and present four surfaces that have the same angular relationship to each other that the surfaces of the metatarsal templates and the surfaces of a resected metatarsal bone have. The selected one of the gauges is positioned over the resected surfaces of the metatarsal bone and is centered laterally on the bone. A centering hole is provided through the gauge. A center hole is drilled into the resected end of the metatarsal bone by drilling through the centering hole of the gauge.

The specialized tools also include a set of three head member punches ranging in sizes of small, medium and large. The selected punch is positioned at the previously drilled centering hole in the resected end of the metatarsal bone and is then impacted into the center of resected end of the metatarsal bone to produce a trapezoid shaped hole that is 10% smaller than the size of the stem of the selected head member. This completes the preparation of the phalanx and metatarsal bone of the joint for implantation of the prosthetic joint of the invention.

BRIEF DESCRIPTION OF THE DRAWINGS

Further objects and features of the present invention are revealed in the following detailed description of the preferred embodiment of the invention and in the drawing figures wherein.

DETAILED DESCRIPTION OF THE PREFERRED EMBODIMENT

Figures 1, 2, 3, 4, 8:
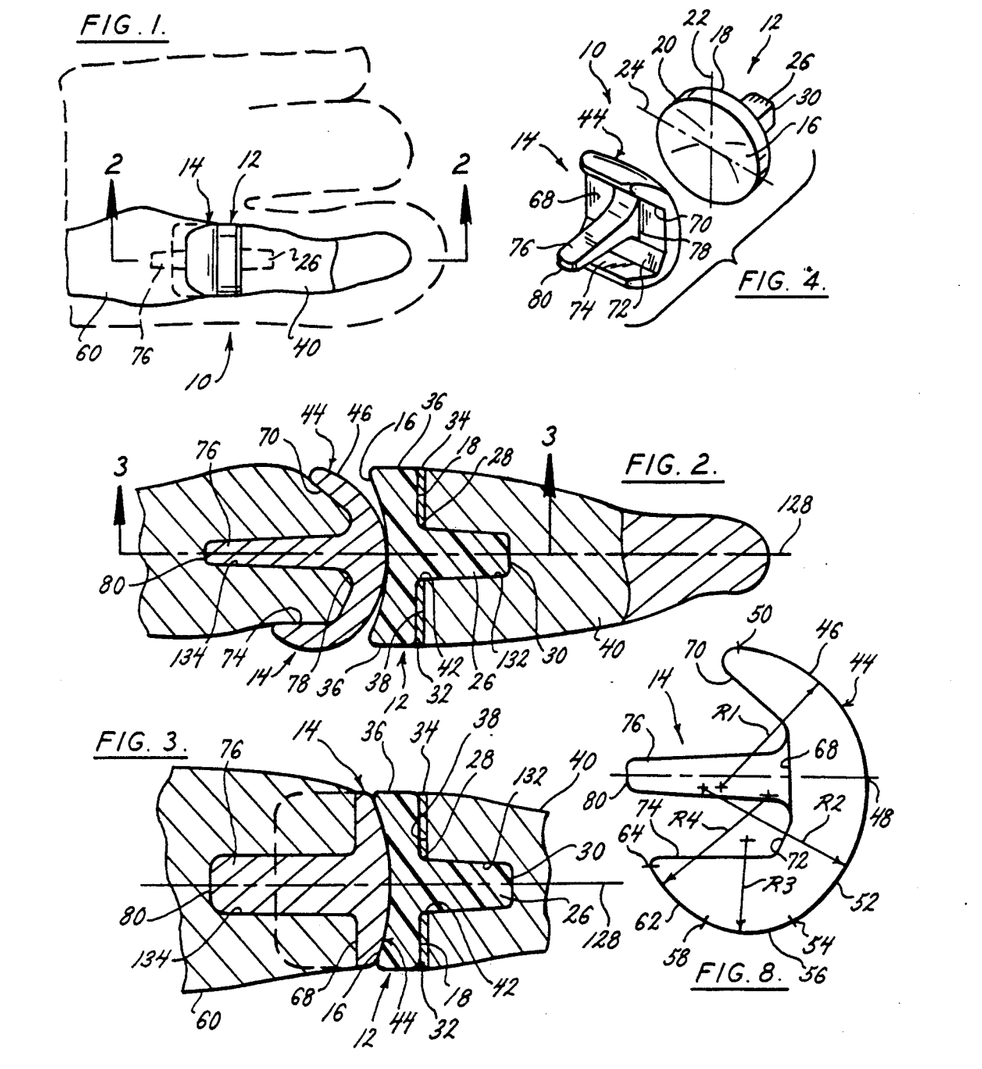
FIG. 1 shows a plan view of the prosthetic joint of the present invention in its implanted position relative to a metatarsal-phalangeal articulation of a human toe.
FIG. 2 shows a section view of the prosthetic joint of the present invention in its implanted position taken along line 2—2 of FIG. 1.
FIG. 3 shows a section view of the implanted prosthetic joint of the present invention taken along line 3—3 of FIG. 2.
FIG. 4 shows an isometric view of the head member and base member of the prosthetic joint of the present invention.
FIG. 8 shows an enlarged side view of the head member, with illustrations showing radii of curvature for the convex surface thereof.
Figure 5:
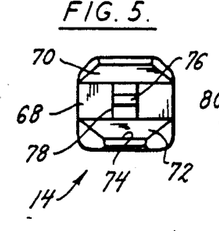
FIG. 5 shows an end view of the head member of the prosthetic joint of the invention.
Figure 6:
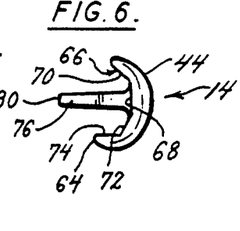
FIG. 6 shows a side view of the head member of the prosthetic joint of the present invention.
Figure 7:
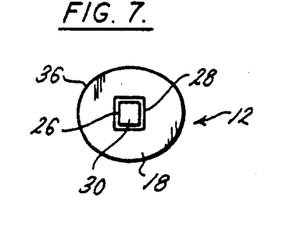
FIG. 7 shows an end view of the base member of the prosthetic joint of the present invention.

The prosthetic joint of the present invention is shown in its implanted position relative to a metatarsal-phalangeal articulation of a human toe in FIG. 1. The prosthetic joint 10 ranges in sizes of small, medium or intermediate, and large, and is comprised of two components, a distally located phalangeal component or base member 12 and a proximally located metatarsal component or head member 14.

The base member 12 has an elliptical shape with a concave bearing surface 16 on one side, and a flat bone confronting surface 18 on the opposite side. The elliptical outer boundary 20 of the concave bearing surface 16 is planar. The concave surface 16 has a first radius of curvature along the vertical minor axis 22 of the ellipse, and a second radius of curvature along the horizontal major axis 24 of the ellipse. The approximate length of radii of curvature for the first and second radii respectively, are now given for three different sizes of base members, smaller, intermediate, and larger: smaller—0.72 in. (1.83 cm.) and 0.94 in. (2.39 cm.); intermediate—0.79 in. (2.01 cm.) and 1.00 in. (2.54 cm.); and larger—0.88 in. (2.26 cm.) and 1.13 in. (2.87 cm). The ratio of the length of the first radius to the second radius is about 0.77, and preferably within a range of 0.73 to 0.81. The bone confronting surface 18 of the base member 12 opposite the bearing surface 16 is planar and arranged to extend perpendicular to the longitudinal axis of a phalanx bone implanted with the base member 12. A base member stem 26 protrudes integrally and distally from the center of the bone confronting surface 18. The base member stem 26 has a square cross section and is tapered from its connection 28 with the bone confronting surface 18 of the base member 12 to its distal end 30. A titanium spacer 32 having an outer boundary 34 that is co-extensive to the elliptical outer boundary 36 of the base member 12 is provided distally on the bone confronting surface 18. The spacer 32 is to be positioned between the bone confronting surface 18 of the base member 12 and a resected surface 38 of a phalanx bone 40. The spacer 32 has a hole 42 at its center to receive the base stem 26.

The metatarsal component or head member 14 of the prosthetic joint 10 has a distally facing convex bearing surface 44. The surface 44 is shaped to permit sliding movement of the concave bearing surface 16 of the base member 12 over the entire bearing surface 44. In particular, the surface 44 permits an extended range of vertical sliding movement of the base member 12 over the convex bearing surface 44. The convex bearing surface 44 is a blend of four separate surface areas into a smooth and continuous curved surface. Referring to FIG. 8, the first surface area 46 extends from a mid line or central axis 48 across the width of the bearing surface 44 upward along the dorsal side of surface 44 to the top edge 50 of the bearing surface 44. Surface 46 permits an extended range of movement of the base member 12 horizontally up over the bearing surface 44 and enables the prosthetic joint to emulate the natural pivoting movement of the phalanx bone relative to the metatarsal bone in a healthy toe joint. The second bearing surface area 52 begins at the mid line 48 of the bearing surface 44 and extends downwardly along the plantar side of the bearing surface 44 to a line 54 where the bearing surface begins its horizontal inclination that forms the bottom most portion of the plantar side of the bearing surface 44. The third bearing surface area 56 forms the bottom most portion of the plantar side of the bearing surface 44 and receives the forces transmitted to the head member 14 of the prosthetic joint by walking. The third bearing surface area extends from the line 54 where substantial horizontal inclination of the bearing surface 44 on the plantar side begins, to the line 58 where the curvature of the bottom of the bearing surface 44 toward the resected metatarsal 60 begins. The fourth bearing surface area 62 extends from the line 58 along the plantar side of surface 44 to the rearward most edge 64 of surface 44 that lies adjacent to a resected surface of the metatarsal bone 60.

Figures 9, 10, 11, 12:
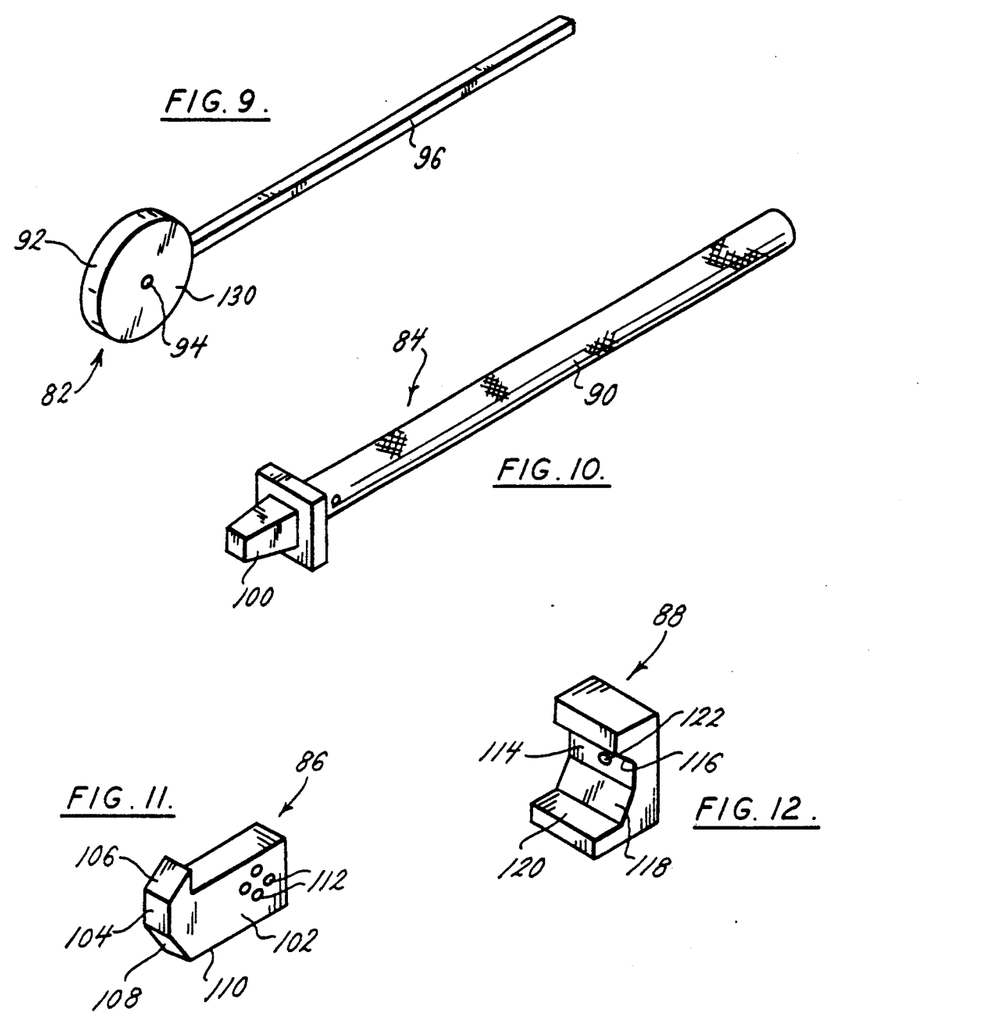
FIG. 9 shows an isometric view of a phalanx template of the set of specialized tools of the present invention.
FIG. 10 shows an isometric view of a phalanx broach of the set of specialized tools of the present invention.
FIG. 11 shows an isometric view of a metatarsal template of the set of specialized tools of the present invention.
FIG. 12 shows an isometric view of a metatarsal resection gauge of the set of specialized tools of the present invention.

Each of the four bearing surface areas 46, 52, 56, 62, have different radii of curvature R1, R2, R3 and R4, and are all blended together to form a continuous curved bearing surface 44. As seen in FIG. 9, each radii R1, R2, R3 and R4 have different centers, each of which is shown by a "+". Each center is shown lying on the plantar side of the central axis or mid line 48, or beneath the central axis or mid line 48. The center of radius R3 is shown located substantially beneath, or to the plantar side, the centers of the radii of each of R1, R2 and R4. The center of radius R4 is closer to the intersection of central axis 48 with surface 44, or is more distally located, than are either the centers of radii R1, R4 or R3. The center of radius R2 is located farthest from, or more proximally from the intersection of central axis 48 with surface 44, as compared to the centers of radii R1, R3 and R4.

The approximate lengths of each radii are now given for three different size head members 14, smaller, intermediate and larger, which sizes correspond to the same designations given for the base member. For a smaller size head member: R1=0.35 In. (0.89 cm); R2=0.41 In. (1.04 cm); R3=0.20 In. (0.50 cm); and R4=0.35 In. (0.89 cm). For an intermediate size head member: R1=0.39 In. (0.99 cm); R2=0.45 In. (1.14 cm); R3=0.22 In. (0.56 cm); and R4=0.39 In. (0.99 cm). For a larger size head member: R1=0.43 In. (1.09 cm); R2=0.49 In. (1.24 cm); R3=0.24 In. (0.61 cm); and R4=0.43 In. (1.09 cm).

The ratios are preferably approximately: R1/R2=0.87, R1/R3=1.82; R1/R4=1.1 and R2/R3=2.1. The ratios preferably lie with the following approximate ranges R1/R2—0.80 to 0.94; R1/R3—1.75 to 1.9; R1/R4—1.0 to 1.3; and R2/R3—1.8 to 2.4.

The concave bone confronting surface 66 of the head member 14 is comPrised of four separate planar surface areas. A first surface area 68 of the bone confronting surface 66 of the head member is arranged to extend perpendicular to the longitudinal axis of a metatarsal bone implanted with the head member 14 of the prosthetic joint. The second surface area 70 extends above and back from the first surface area 68 at an angle of about 35° to overlap a dorsal portion of a resected metatarsal bone implanted with the prosthetic joint. Preferably the said angle to between 32° and 38°. The third surface area 72 extends downward and back from the first surface area 68 at an angle of about 65°, below a plantar portion of a resected metatarsal bone implanted with the prosthetic joint. Preferably the said angle is between 62° and 68°. The fourth surface area 74 extends horizontally from the third surface area 72 to the rearward most edge 64 of the head member bearing surface 44. Surface area 74 is approximately parallel to central axis 48 and approximately perpendicular to surface 68. The horizontal fourth surface area 74 is arranged to confront a horizontally resected portion of a metatarsal bone implanted with the prosthetic joint. The fourth surface area 74 distributes a vertical force component of the forces acting on the third bearing surface area 56 of the head member 14 from walking over an increased horizontal area of the metatarsal bone. The four surface areas of the bone confronting surface 66 of the head member 14 are all planar surfaces and provide a mutually confronting surface connection between the bone confronting surface 66 of the head member 14 and the resected surfaces of a metatarsal bone 60 implanted with the prosthetic joint 10.

A head member stem 76 protrudes integrally from the first surface area 68 of the bone confronting surface 66 of the head member. The head stem 76 is perpendicular to the first surface area 68 and is arranged to extend parallel to the longitudinal axis of a metatarsal bone implanted with the prosthetic joint. The head stem 76 has a rectangular cross section and is tapered from its connection 78 to the first surface area 68 to its distal end 80.

A specialized set of tools is required to prepare the phalanx and metatarsal bones of a toe joint for the implantation of the base member and head member respectively, of the prosthetic joint of the invention. These specialized tools are shown in FIGS. 8 through 12 and include a phalanx template 82, a phalanx broach 84, a metatarsal template 86, a metatarsal resection gauge 88, and a metatarsal broach 90. Each of the five specialized tools listed above comes in sizes of small, medium and large. A set of tools of one size is chosen for the resection of the phalanx and metatarsal bones of the toe joint being replaced dependent on the size of the prosthetic joint chosen to be implanted on the phalanx and metatarsal bones.

The phalanx template 82 has an elliptical outer surface 92 that is equivalent in size to the elliptical outer surface 36 of the base member 12 chosen to be implanted on the phalanx bone. A center hole 94 is provided at the center of the template 82. A handle 96 is provided extending from a side of the template 82 to facilitate the positioning of the template at the resected end of a phalanx bone being prepared for the implantation of the base member 12.

The phalanx broach 84 comprises a rod member 98 with a trapezoid shaped broach 100 at one end of the rod 98. The dimensions of the broach 100 are 10% smaller than the dimensions of the base stem 26 of the prosthetic joint base member 12 chosen to be implanted on the phalanx bone. This insures a secure fit of the base member on the resected end of the phalanx bone.

The metatarsal template 86 comprises a rectangular base section 102 having four guide surfaces 104, 106, 108, 110, on one end of the rectangular base. The four guide surfaces 104, 106, 108, 110, correspond to the four surface areas 68, 70, 72, 74, of the concave bone confronting surface 66 of the head member 14 chosen to be implanted on the resected end of the metatarsal bone 60. A series of pin holes 104 are provided through the rectangular base section 102 of the metatarsal template. The pin holes enable the template to be pinned to a side of the metatarsal bone 60 so that the metatarsal bone can be resected across the four guide surfaces 104, 106, 108, 110. Resection of the bone across the four guide surfaces produces four resected surfaces on the end of the metatarsal bone that will mutually confront the four surface areas 68, 70, 72, 74, respectively of the head member 14 of the prosthetic joint to be implanted on the metatarsal bone.

The metatarsal resection gauge 88 also comprises four planar surfaces 114, 116, 118, 120. The four surfaces correspond to the four guides surfaces 104, 106, 108, 110 respectively, of the metatarsal template 86 and the four planar resected surfaces cut in the end of a metatarsal bone 60 by using the template 86. The four surfaces on the metatarsal resection gauge 88 are provided as a check for the resected surfaces of the metatarsal bone 60. The gauge 88 ensures that the resected surfaces of the metatarsal bone will confront the four surface areas 68, 70, 72, 74, of the head member 14 to be implanted on the metatarsal bone 60. A center hole 122 is also provided through the metatarsal resection gauge 88. The centering hole is centered in the first surface 114 of the resection gauge 88 and extends through the resection gauge perpendicular to the first guide surface 114.

Figure 13:
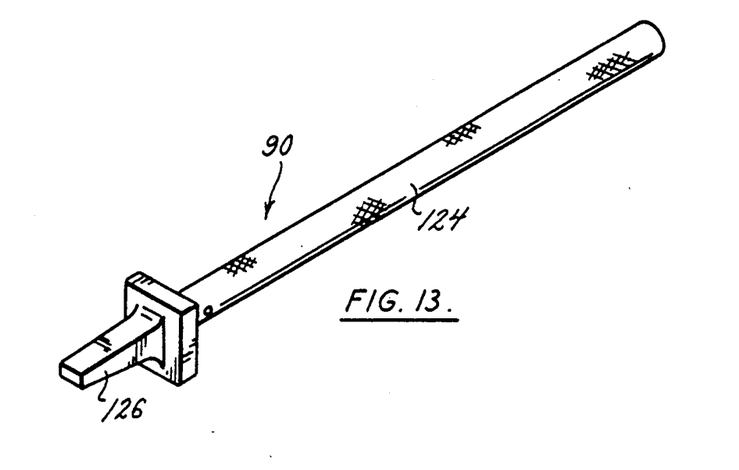
FIG. 13 shows an isometric view of a metatarsal broach of the set of specialized tools of the present invention.

The metatarsal broach 90 comprises a rod member 124 and a broach 126 at one end of the rod. The broach 126 has a trapezoid shape and is dimensioned 10% smaller than the size of the head member stem 76 of the prosthetic joint head member 14 chosen for implantation on the end of the resected metatarsal bone 60. This permits the head member 14 to be press fit and secured onto the end of a resected metatarsal bone 60.

In preparing to replace a metatarsal-phalangeal articulation of a human toe with the prosthetic joint of the present invention, a properly sized small, medium or large prosthetic joint must first be chosen depending on the size of the metatarsal and phalangeal bones of the toe joint being replaced. From the desired size of prosthetic joint chosen, the proper sized, small, medium, or large, set of specialized tools for preparation of the metatarsal and phalanx bones is chosen.

The first step involved in the preparation of the metatarsal and phalanx bones for the implantation of the chosen prosthetic joint involves the resection of the joint end of the phalanx bone 40. The joint end of the phalanx bone 40 is resected to present a planar surface 38 that is perpendicular to the longitudinal axis 128 of the phalanx bone 40. The smooth surface 130 of the phalanx template 82 is positioned against the resected surface 38 of the phalanx 40 to insure that the resected surface 38 is planar. The outer circumferential surface 92 of the template is dimensioned identical to the outer circumferential surface 36 of the base member 12 to be implanted on the phalanx bone 40. The surface 92 is used as a guide in the resection of the outer circumferential surface of the phalanx bone so that the outer resected surface of the phalanx bone 40 forms a continuous smooth surface with the outer surface 36 of the base member 12 implanted on the phalanx bone. Following the resection of the phalanx bone to match the surfaces 92, 130 of the phalanx template 82, a center pilot hole is drilled into the phalanx bone 40. The hole is made by drilling through the center hole 94 of the phalanx template 82 that is properly positioned on the resected surface 38 of the phalanx bone 40. By properly positioning the phalanx template 82 on the resected surface 38 of the phalanx bone 40, the hole drilled into the phalanx bone will extend coaxial to the longitudinal axis of the bone.

Following the drilling of the pilot hole into the center of the phalanx bone 40, the phalanx broach 84 is impacted into the pilot hole to drive the broach 80 into the center of the phalanx bone 40. The impaction of the broach 100 into the pilot hole produces a cavity 132 in the resected end of the phalanx bone 40 having a trapezoid shape corresponding to the shape of the broach 100. The cavity 132 produced is coaxial to the axis 128 of the phalanx bone 40. With the joint end of the phalanx bone 40 resected to present a planar surface 38 perpendicular to the axis 128 of the bone, and the phalanx cavity 132 formed in the resected end of the phalanx bone 40, the bone is prepared for implantation of the base member 12 of the prosthetic joint 10.

The base member 12 of the prosthetic joint 10 is next implanted on the resected end of the phalanx bone 40. The base member 12 is oriented relative to the phalanx bone 40 in the positions shown in FIGS. 2 and 3. The horizontal major axis 24 of the concave bearing surface 16 of the base member and the vertical minor axis 22 of the concave bearing surface of the base member are both positioned perpendicular to the longitudinal axis 128 of the phalanx bone 40. The base stem 26 is inserted into the phalanx cavity 132 and the base member 12 is press fit on the resected end of the phalanx bone 40 until the titanium spacer 34 abuts against the resected surface 38 of the bone and the flat surface 18 of the base member 12. The base stem 26, being 10% larger than the phalanx cavity 132, is press fit into the cavity to provide a secure connection between the phalanx bone 40 and the base member 12 of the prosthetic joint 10 without the use of cement.

The joint end of the metatarsal bone 60 is next prepared for the implantation of the head member 14 of the prosthetic joint 10. The metatarsal template 86 is first positioned at a side of the metatarsal bone 60 with the fourth guide surface 110 extending parallel to the longitudinal axis 128 of the metatarsal bone 60. The metatarsal template is then secured in this position relative to the metatarsal bone 60 by passing pins through the pin holes 112 through the base section 102 and into the metatarsal bone 60. The end of the metatarsal bone 60 is then resected to present four planar surfaces that are coplanar with the guide surfaces 104, 106, 108, 110, of the metatarsal template 86.

Following the resection of the end of the metatarsal bone, the metatarsal template 86 is removed from the bone and the metatarsal resection gauge 88 is placed over the resected end of the bone. The metatarsal resection gauge 88 is placed on the end of the resected metatarsal bone 60 to check whether the four resected surfaces of the metatarsal bone match up with the four guide surfaces 114, 116, 118, 120, of the metatarsal gauge 88. The resection gauge 88 ensures that the four resected surfaces of the metatarsal bone are planar and are properly positioned relative to each other to provide smooth confronting surfaces for the four surface areas 68, 70, 72, 74, of the bone confronting surface 66 of the head member 14. Following the check of the resected metatarsal surfaces, a pilot hole is drilled into the metatarsal bone by drilling through the center hole 122 through the metatarsal resection gauge 88. The pilot hole drilled extends coaxial to the longitudinal axis 128 of the metatarsal bone 60.

Following the drilling of the pilot hole in the end of the metatarsal bone 60, the resection gauge 88 is removed and the broach end 126 of the metatarsal broach 90 is impacted into the pilot hole. The metatarsal broach 90 forms a metatarsal cavity 134 coaxial to the longitudinal axis 128 of the metatarsal bone 60 and dimensioned 10% smaller than the head member stem 76 of the head member 14 chosen for implantation on the resected metatarsal bone. With this metatarsal cavity 134 formed in the resected end of the metatarsal bone 60, the bone is prepared for the implantation of the head member 14 of the prosthetic joint 10.

The head member 14 of the prosthetic joint 10 is next implanted on the resected end of the metatarsal bone 60. The head member 14 is oriented relative to the metatarsal bone in the positions shown in FIGS. 2 and 3. The head stem 76 is first inserted into the metatarsal cavity 134 formed in the resected end of the bone 60. The head member 14 is then press fit onto the resected end of the metatarsal bone 60 so that the first, second, third and fourth surface areas 68, 70, 72, 74, of the concave bone confronting surface 66 of the head member engage with the four resected surfaces of the metatarsal that have been cut to conform with the guide surfaces 104, 106, 108, 110 respectively of the metatarsal template 86. The mutual contact between the surface areas of the bone confronting surface 66 of the head member and the resected surfaces on the end of the metatarsal insure that the head member remains in its position relative to the metatarsal and is not twisted out of position by the torsion forces exerted on the head member from walking. The dimensions of the head member stem 76 are 10% larger than the metatarsal cavity 134. This insures that the head member 14 remains secured in its position implanted on the end of the resected metatarsal 60 without the use of cement.

In the implanted position on the resected end of the metatarsal 60, the prosthesis joint head member 14 provides a horizontal area of surface contact 74 between the head member and the resected metatarsal. Forces exerted on the bottom surface area 56 of the bearing surface 44 of the head member will be transmitted to the resected metatarsal 60 as a vertical component of force and a horizontal component of force. The effect of the vertical component of force on the metatarsal is lessened by the horizontal fourth surface area 74 of the head member 14. This surface distributes the force over an increased horizontal area of the resected metatarsal 60. The fourth surface area 74 confronting the metatarsal bone 60 also has an effect on the horizontal component of force exerted on the head member 14. The force resisting horizontal movement of the head member due to the contact between the fourth surface area 74 of the head member 14 and the confronting area of the resected metatarsal bone is increased by providing an increased horizontal area of mutual contact. The resisting force between the head member 12 and the resected bone acts parallel to the fourth surface area 74 of the bone confronting surface 66 of the head member 14 and resists the horizontal component of force acting on the head member 12. This reduces the magnitude of the horizontal component of force that would tend to separate the head member from the resected toe.

While the present invention has been described by reference to a specific embodiment, it should be understood that modifications and variations of the invention may be constructed without departing from the scope of the invention defined in the following claims.

What is claimed is:

1. A prosthetic joint for replacing a metatarsal-phalangeal articulation of a human toe comprising:
    a head member shaped to be surgically implanted at an end of a metatarsal bone of the articulation, the head member having a convex bearing surface and a concave bone confronting surface shaped to be secured to a resected end of a metatarsal bone of the articulation;
    a base member shaped to be surgically implanted at an end of a phalanx bone of the articulation, the base member having a concave bearing surface arranged to slide over the convex bearing surface of the head member, and a bone confronting surface arranged to be secured to a resected end of a phalanx bone of the articulation; and
    the concave bone confronting surface of the head member having a substantially flat plantar surface section that is oriented with respect to the rest of the bone confronting surface so that it extends substantially parallel to the longitudinal axis of a metatarsal bone implanted with the head member, and is positioned to contact a horizontal resected area beneath the implanted metatarsal bone.

2. The prosthetic joint of claim 1 comprising:
    the head member being a unitary piece and the base member being a unitary piece.

3. A prosthetic joint for replacing a metatarsal-phalangeal articulation of a human toe comprising:
    a head member shaped to be surgically implanted at an end of a metatarsal bone of the articulation, the head member having a convex bearing surface and a concave bone confronting surface shaped to be secured to a resected end of a metatarsal bone of the articulation, the bearing surface of the head member having four surface portions arranged so that a center line extending over the bearing surface through the four portions forms a continuous curve having four different radii of curvature;
    a base member shaped to be surgically implanted at an end of a phalanx bone of the articulation, the base member having a concave bearing surface arranged to slide over the convex bearing surface of the head member, and a bone confronting surface arranged to be secured to a resected end of a phalanx bone of the articulation; and
    the concave bone confronting surface of the head member having a substantially flat plantar surface section that is oriented with respect to the rest of the bone confronting surface so that it extends substantially parallel to the longitudinal axis of a metatarsal bone implanted with the head member, and is positioned to contact a horizontal resected area beneath the implanted metatarsal bone.

4. The prosthetic joint of claim 1 comprising:
    the bone confronting surface of the head member having at least four planar sections.

5. The prosthetic joint of claim 1 comprising:

the head member having a longitudinal central axis for alignment with the longitudinal metatarsal bone axis, and the bone confronting surface of the head member having a planar section extending substantially perpendicular to the longitudinal axis of the head member.

6. The prosthetic joint of claim 1 wherein the head member has a longitudinally extending central axis for alignment with a longitudinal axis of the metatarsal bone, the bone-confronting surface of the head member has a dorsal surface extending at an angle of about 35° relative to the central axis of the head member.

7. The prosthetic joint of claim 1 wherein the head member has a longitudinally extending central axis for alignment with a longitudinal axis of the metatarsal bone, the bone-confronting surface of the head member has a downwardly extending plantar surface extending at an angle of about 65° relative to the central axis of the head member.

8. The prosthetic joint of claim 5 comprising:
second and third planar sections of the bone confronting surface of the head member being arranged to extend from above and below the first planar section respectively, at angles to the longitudinal axis of the head member.

9. The prosthetic joint of claim 5 comprising:
a head member stem protruding proximally from the planar section that is substantially perpendicular, the head stem having an axis that aligned with the central axis of the head member and positioned to be inserted into a hole bored into a resected end of a metatarsal bone to secure the head member to the bone.

10. The prosthetic joint of claim 1 comprising:
the bearing surface of the base member having an elliptical, planar outer boundary, the surface having a first radius of curvature along a vertical axis of the surface and having a second radius of curvature, greater than the first radius of curvature, along a horizontal axis of the surface.

11. The prosthetic joint of claim 10 comprising:
the ratio of the first radius of curvature to the second radius of curvature being about 0.77.

12. A prosthetic joint for replacing a metatarsal-phalangeal articulation of a human toe comprising:
a head member shaped to be surgically implanted at an end of a metatarsal bone of the articulation, the head member having a convex bearing surface and a concave bone confronting surface shaped to be secured to a resected end of a metatarsal bone of the articulation;
a base member shaped to be surgically implanted at an end of a phalanx bone of the articulation, the base member having a concave bearing surface arranged to slide over the convex bearing surface of the head member, and a bone confronting surface arranged to be secured to a resected end of a phalanx bone of the articulation;
the concave bone confronting surface of the head member having a plantar surface section that is oriented with respect to the rest of the bone confronting surface so that it extends substantially parallel to the longitudinal axis of a metatarsal bone implanted with the head member, and is positioned to contact a horizontal resected area beneath the implanted metatarsal bone; and
the bearing surface of the base member having an elliptical, planar outer boundary, the surface having a first radius of curvature along a vertical axis of the surface and having a second radius of curvature, greater than the first radius of curvature, along a horizontal axis of the surface, the ratio of the first radius of curvature to the second radius of curvature being in the range of about 0.73 to about 0.81.

13. The prosthetic joint of claim 10 comprising:
the bone confronting surface of the base member having a section that is substantially flat, and a base member stem protruding distally from and integrally with the substantially, flat section of the bone confronting surface of the base member, the base stem having an axis that is substantially perpendicular to the substantially flat section and being positioned to be inserted into a hole bored into a resected end of a phalanx bone to secure the base member to the bone.

14. The prosthetic joint of claim 9 comprising:
the head stem having a rectangular cross section and being tapered from its connection to the surface of the bone confronting surface of the head member to its distal end.

15. The prosthetic joint of claim 13 comprising:
the base stem having a rectangular cross section and being tapered from its connection to the substantially flat section of the bone confronting surface of the base member to its distal end.

16. A prosthetic joint for replacing a metatarsal-phalangeal articulation of a human toe comprising:
a head member shaped to be surgically implanted at an end of a metatarsal bone of the articulation, the head member having a convex bearing surface and a bone confronting surface arranged to be secured to a resected end of a metatarsal bone of the articulation;
a base member shaped to be surgically implanted at an end of a phalanx bone of the articulation, the base member having a concave bearing surface arranged to slide over the convex bearing surface of the head member, and a bone confronting surface for securing to a resected end of a phalanx bone of the articulation; and p1 the convex bearing surface of the head member having at least three surface portions arranged so that a center line extending over the bearing surface through the three portions forms a curve having three different radii of curvature.

17. A prosthetic joint for replacing a metatarsal-phalangeal articulation of a human toe comprising:
a head member shaped to be surgically implanted at an end of a metatarsal bone of the articulation, the head member having a convex bearing surface and a bone confronting surface arranged to be secured to a resected end of a metatarsal bone of the articulation;
a base member shaped to be surgically implanted at an end of a phalanx bone of the articulation, the base member having a concave bearing surface arranged to slide over the convex bearing surface of the head member, and a bone confronting surface for securing to a resected end of a phalanx bone of the articulation; and
the convex bearing surface of the head member having at least three surface portions arranged so that a center line extending over the bearing surface through the three portions forms a curve having three different radii of curvature, the bearing surface of the head member having a dorsal portion with a first radius of curvature, and a plantar portion with a second radius of curvature of different length than the first radius and having a different center than the first radius.

18. The prosthetic joint of claim 17 comprising:
the bearing surface of the head member having a third surface portion on the plantar side of the bearing surface with a third radius of curvature having a center which is located substantially beneath the centers of the first and second radii of curvature, and being of a shorter length than the first and second radii of curvature.

19. The prosthetic joint of claim 17 comprising:
the ratio of the lengths of the first radius to the second radius being within the range of 0.80 to 0.94.

20. The prosthetic joint of claim 18 comprising:
the ratio of the lengths of the first radius to the third radius being within the range of about 1.75 to about 1.9.

21. The prosthetic joint of claim 18 comprising:
the ratio of the lengths of the second radius to the third radius being within the range of about 1.8 to about 2.4.

22. The prosthetic joint of claim 17 comprising:
the ratio of the lengths of the first radius to the second radius being approximately 0.87.

23. The prosthetic joint of claim 18 comprising:
the ratio of the lengths of the first radius to the third radius being approximately 1.82.

24. The prosthetic joint of claim 18 comprising:
the ratio of the lengths of the second radius to the third radius being approximately 2.1.

25. The prosthetic joint of claim 18 comprising:
the bearing surface of the head member having a fourth surface portion lying proximal to the third surface portion, and having a fourth radius of curvature whose center is different from the center of the first, second and third radius of curvature, and whose length is longer than the length of the third radius of curvature.

26. The prosthetic joint of claim 25 comprising:
the ratio of the lengths of the first radius to the fourth radius ranging from about 1.0 to about 1.3.

27. The prosthetic joint of claim 25 comprising:
the ratio of the lengths of the first radius to the fourth radius being approximately 1.1.

28. The prosthetic joint of claim 16 comprising:
the head member being a unitary piece and the base member being a unitary piece.

29. The prosthetic joint of claim 16 comprising:
the head member having a longitudinal central axis, and the bone confronting surface of the head member having at least four planar sections extending across its width.

30. The prosthetic joint of claim 29 comprising:
a first planar section of the bone confronting surface of the head member being arranged to extend substantially perpendicular to the longitudinal central axis of the head member.

31. The prosthetic joint of claim 30 comprising:
second and third planar sections of the bone confronting surface of the head member extending from above and below the first planar section respectively at angles to the longitudinal central axis of the head member.

32. The prosthetic joint of claim 29 comprising:
one of the four planar sections of the bone confronting surface of the head member extending substantially parallel to the longitudinal central axis of the head member along the plantar side of the head member to contact the plantar side of the resected end of the phalanx bone.

33. The prosthetic joint of claim 16 comprising:
the bearing surface of the base member having an elliptical, planar outer boundary, the surface having a first radius of curvature along a vertical axis of the surface and having a second radius of curvature, greater than the first radius of curvature, along a horizontal axis of the surface.

34. A prosthetic join for replacing a metatarsalphalangeal articulation of a human toe comprising:
a one-piece head member shaped to be surgically implanted at an end of a metatarsal bone of the articulation;
a one-piece base member shaped to be surgically implanted at an end of a phalanx bone of the articulation;
the head member having a convex bearing surface and a concave bone confronting surface, the bearing surface being so arranged that a center line extending vertically over the bearing surface forms a continuous curve of four different radii of curvature, and the bone confronting surface having a first surface section arranged to extend substantially perpendicular to a longitudinal axis of a metatarsal bone implanted with the head member and to abut against a resected end of the bone, second and third surface sections arranged to extend from above and below the first surface section respectively, at angles to a longitudinal axis of an implanted metatarsal bone, and a fourth surface section arranged to extend substantially parallel to the longitudinal axis of an implanted metatarsal bone;
the base member having a concave bearing surface and a flat bone confronting surface, the concave bearing surface being arranged to slide over the convex bearing surface of the head member, and the bone confronting surface being arranged to extend substantially perpendicular to a longitudinal axis of a phalanx bone implanted with the base member and to about against a resected end of the bone;
a head member stem protruding from the first surface section of the bone confronting surface of the head member, the head stem having an axis that is perpendicular to the first surface section, the head stem being arranged to be inserted into a hole bored into a resected end of a metatarsal bone to secure the head member to the bone; and
a base member stem protruding from the flat bone confronting surface of the base member, the base stem having an axis that is perpendicular to the flat surface, the base stem being arranged to be inserted into a hole bored into a resected end of a phalanx bone to secure the base member to the bone.

35. A prosthetic joint for replacing a metatarsalphalangeal articulation of a human toe comprising:
a head member shaped to be surgically implanted at an end of a metatarsal bone of the articulation, the head member having a convex bearing surface and a concave bone confronting surface shaped to be secured to a resected end of a metatarsal bone of the articulation, the bone confronting surface of the head member having a substantially flat plantar surface section that is oriented with respect to the rest of the bone-confronting surface so that it extends substantially horizontally and substantially parallel to the longitudinal axis of a metatarsal bone implanted with the head member, the said substantially horizontal surface being positioned to contact a horizontal resected area located at the bottom of the implanted metatarsal bone, the head member being a unitary piece, with the bearing surface of the head member having thee surface portions arranged so that a center line extending over the bearing surface across the portions forms a continuous curve having three different radii of curvature.

36. The prosthetic joint of claim 35 wherein the bearing surface of the base member has a surface with a first radius of curvature along a vertical axis of the surface, and a second radius of curvature greater than the first radius of curvature along a horizontal axis, with the ratio of the first radius of curvature of the second radius of curvature being about 0.77.

37. A prosthetic joint for replacing a metatarsal-phalangeal articulation of a human toe comprising:
a head member shaped to be surgically implanted at an end of a metatarsal bone of the articulation, the head member having a convex bearing surface having two surface portions arranged so that a center line extending across the portions forms a continuous curve having first and second radii of curvature, the said radii of curvature being different from one another, the ratio of the first radius to the second radius being within the range of about 0.80 to about 0.94, the head member having a concave bone confronting surface shaped to be secured to a resected end of a metatarsal of the articulation.

* * * * *

UNITED STATES PATENT AND TRADEMARK OFFICE
CERTIFICATE OF CORRECTION

PATENT NO. : 5,037,440
DATED : August 6, 1991
INVENTOR(S) : Richard B. Koenig

It is certified that error appears in the above—identified patent and that said Letters Patent is hereby corrected as shown below:

Column 2, line 64, "Perpen-" should be --perpen--;

Column 4, line 13, "a" should be -- an --;

Column 7, line 68, "comPrised" should be -- comprised --;

Column 14, line 43 (claim 16), "p1" should be deleted and the words "the convex bearing ..." should be at the beginning of a new paragraph Column 16, line 45 (claim 34), "about" should be -- abut --.

Signed and Sealed this

Twelfth Day of January, 1993

Attest:

DOUGLAS B. COMER

*Attesting Officer*     Acting Commissioner of Patents and Trademarks